(12) United States Patent
Tenengauzer et al.

(10) Patent No.: US 6,689,384 B2
(45) Date of Patent: Feb. 10, 2004

(54) STABLE PERGOLIDE MESYLATE AND PROCESS FOR MAKING SAME

(75) Inventors: Ruth Tenengauzer, Hod Hasharon (IL); Minutza Leibovici, Netanya (IL)

(73) Assignee: Teva Pharmaceuticals Industries Ltd., Petah Tiqva (IL)

( * ) Notice: Subject to any disclaimer, the term of this patent is extended or adjusted under 35 U.S.C. 154(b) by 100 days.

(21) Appl. No.: 09/923,499

(22) Filed: Aug. 7, 2001

(65) Prior Publication Data

US 2002/0054904 A1 May 9, 2002

Related U.S. Application Data

(60) Provisional application No. 60/223,774, filed on Aug. 8, 2000.

(51) Int. Cl.[7] ............................. A61K 9/14; A61K 9/20
(52) U.S. Cl. ...................... 424/464; 424/465; 424/489
(58) Field of Search ............................... 424/464, 465, 424/489

(56) References Cited

U.S. PATENT DOCUMENTS

| | | | |
|---|---|---|---|
| 4,797,405 A | | 1/1989 | Conine et al. |
| 5,114,948 A | * | 5/1992 | Conine et al. .............. 514/288 |
| 5,523,082 A | * | 6/1996 | Corbiere ................... 424/78.04 |
| 6,316,027 B1 | * | 11/2001 | Johnson et al. ............. 424/464 |

FOREIGN PATENT DOCUMENTS

WO  WO 02/11727 A1  2/2002

\* cited by examiner

*Primary Examiner*—Thurman K. Page
*Assistant Examiner*—S. Tran
(74) *Attorney, Agent, or Firm*—Kenyon & Kenyon

(57) ABSTRACT

A formulation and a method for manufacturing pergolide mesylate is disclosed whereby substantially stable pergolide mesylate can be manufactured without having to introduce stabilizing additives.

22 Claims, No Drawings

STABLE PERGOLIDE MESYLATE AND PROCESS FOR MAKING SAME

The instant application claims priority to the U.S. Provisional Application No. 60/223,774, filed Aug. 8, 2000 by the same inventors.

FIELD OF THE INVENTION

The present invention relates to the field of pharmaceuticals and, more particularly, to a formulation and a process of manufacturing stable pergolide mesylate.

BACKGROUND OF THE INVENTION

Pergolide Mesylate is an ergot derivative dopamine receptor agonist at both $D_1$ and $D_2$ receptor sites. Pergolide mesylate is chemically designated as 8(beta)-[(Methylthio)methyl]-6-propylergoline monomethanesulfonate, and has the following structural formula:

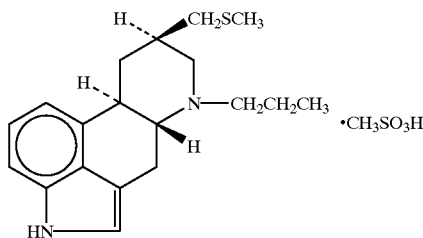

The formula weight of the base is 314.5; 1 mg of base corresponds to 3.18 μmol.

Pergolide Mesylate is sold under the trade name PERMAX® and is provided for oral administration in tablets containing 0.05 mg (0.159 μmol), 0.25 mg (0.795 μmol), or 1 mg (3.18 μmol) pergolide as the base. The tablets also contain croscarmellose sodium, iron oxide, lactose, magnesium stearate, and povidone. The 0.05-mg tablet also contains methionine, and the 0.25-mg tablet also contains F D & C Blue No. 2.

Pharmaceutically, pergolide mesylate is a potent dopamine receptor agonist. Pergolide is 10 to 1,000 times more potent than bromocriptine on a milligram per milligram basis in various in vitro and in vivo test systems. Pergolide mesylate inhibits the secretion of prolactin in humans; it causes a transient rise in serum concentrations of growth hormone and a decrease in serum concentrations of luteinizing hormone. In Parkinson's disease, pergolide mesylate is believed to exert its therapeutic effect by directly stimulating post-synaptic dopamine receptors in the nigrostriatal system.

Information on oral systemic bioavailability of pergolide mesylate is unavailable because of the lack of a sufficiently sensitive assay to detect the drug after the administration of a single dose. However, following oral administration of $^{14}C$ radio-labeled pergolide mesylate, approximately 55% of the administered radioactivity can be recovered from the urine and 5% from expired $CO_2$, suggesting that a significant fraction is absorbed. Data on post absorption distribution of pergolide are unavailable.

Pergolide is approximately 90% bound to plasma proteins. This extent of protein binding may be important to consider when pergolide mesylate is co-administered with other drugs known to affect protein binding.

U.S. Pat. No. 4,797,405 which is incorporated herein by reference discloses that pergolide decomposes upon exposure to light to sulfoxide species. As a result, it is necessary to handle the compound and store the ultimate dosage form in a light-controlled environment so as to avoid a demonstrable drop in potency of the therapeutic agent. In order to retard this drop in potency, certain stabilizing agents have been incorporated into pharmaceutical compositions containing pergolide to reduce decomposition when exposed to light. Each of U.S. Pat. Nos. 4,797,405 and 5,114,948 disclose various stabilizing agents that purportedly retard decomposition to sulfoxide. However, beyond addition of stabilizing additives, the references fail to remedy the decomposition problem.

SUMMARY OF THE INVENTION

The present invention provides for stable pergolide mesylate in dry dosage form and in therapeutically effective amount without the addition of stabilizing compound. A process for manufacturing stable pergolide mesylate is also provided for both dry and wet granulates. The pergolide mesylate compound produced according to the invention is found to be substantially stable even without the presence of stabilizing compounds.

DETAILED DESCRIPTION

The embodiments of the present invention are described according to the following examples. The advantages of the invention are illustrated by way of comparative data in tables that follow.

EXAMPLE 1

Wet Granulation

| A. 0.05 mg Tablets | |
|---|---|
| Pergolide Mesylate | 0.065 mg* |
| Lactose Monohydrate NF | 157.565 mg |
| Microcrystalline Cellulose NF | 80.0 mg |
| Pregelatinized Starch NF | 30.0 mg |
| Sodium Starch Glycolate NF | 30.0 mg |
| Magnesium Stearate NF | 2.25 mg |
| Color Ferric Oxide NF | 0.12 mg |
| Purified Water USP (processing solvent only) | |
| Alcohol USP 95% (processing solvent only) | |
| TOTAL | 300.0 mg |

| B. 0.25 mg Tablets | |
|---|---|
| Pergolide Mesylate | 0.325 mg** |
| Lactose Monohydrate NF | 156.575 mg |
| Microcrystalline Cellulose NF | 80.0 mg |
| Pregelatinized Starch NF | 30.0 mg |
| Sodium Starch glycolate NF | 30.0 mg |
| Magnesium stearate NF | 2.25 mg |
| Color ferric Oxide NF | 0.65 mg |
| Color FDC Blue No. 2 | 0.2 mg |
| Purified Water USP (processing solvent only) | |
| Alcohol USP 95% USP (processing solvent only) | |
| TOTAL | 300.0 mg |

| C. 1.0 mg Tablets | |
|---|---|
| Pergolide Mesylate | 1.3 mg*** |
| Lactose Monohydrate NF | 155.95 mg |
| Microcrystalline Cellulose NF | 80.0 mg |
| Pregelatinized Starch NF | 30.0 mg |
| Sodium Starch Glycolate NF | 30.0 mg |
| Magnesium Stearate NF | 2.25 mg |

-continued

| | |
|---|---|
| Color Ferric Oxide NF | 0.5 mg |
| Purified Water USP (processing solvent only) | |
| Alcohol USP 95% (processing solvent only) | |
| TOTAL | 300 mg |

*Equivalent to 0.05 mg Pergolide base.
**Equivalent to 0.25 mg Pergolide Base.
***Equivalent to 1 mg Pergolide Base.

Lactose monohydrate, microcrystalline cellulose, pregelatinized starch, sodium starch glycolate and the colors were mixed in a high speed mixer. Pergolide mesylate was dissolved in a mixture of purified water and alcohol USP (1:3). The granulation was performed by adding pergolide mesylate solution to the powder mixture. The wet granulation was dried in a fluid bed drier at 50° C., using an air flow of 200–500 m$^3$/h/kg for 30–60 minutes (LOD: 0.5–2.5%). Once dry, the granulates were milled. Thereafter, magnesium stearate was added to the milled granulate and mixed. The final blend was compressed into oval shaped tablets on a rotary tableting machine (batch size ca. 7 Kg tablets).

Stability studies were initiated at accelerated conditions (40° C. and 75% relative humidity) for three months and compared with Permax® (Atena) tablets. The following stability results were obtained:

TABLE 1

Stability study of 0.05 mg pergolide tablets prepared according to the principles of the invention.

| Interval | Assay (%) | Degradation Products (%) Pergolide Sulfoxide | Degradation Products (%) Total (excluding pergolide Sulfoxide) |
|---|---|---|---|
| 0 Mo. | 99.4 | 1.1 | <0.05 |
| 3 Mo. | 94.2 | 4.8 | 1.3 |

TABLE 2

Permax ® (0.05 mg)

| Interval | Assay (%) | Degradation Products (%) Pergolide Sulfoxide | Degradation Products (%) Total (excluding pergolide Sulfoxide) |
|---|---|---|---|
| 0 Mo. | 100.0 | 1.7 | 0.3 |
| 3 Mo. | 95.9 | 3.6 | 0.4 |

TABLE 3

Stability study of 0.25 mg pergolide tablets prepared according to the principles of the invention.

| Interval | Assay (%) | Degradation Products (%) Pergolide Sulfoxide | Degradation Products (%) Total (excluding pergolide Sulfoxide) |
|---|---|---|---|
| 0 Mo. | 103.1 | 0.3 | <0.5 |
| 3 Mo. | 99.3 | 1.3 | 0.5 |

TABLE 4

Permax ® (0.25 mg)

| Interval | Assay (%) | Degradation Products (%) Pergolide Sulfoxide | Degradation Products (%) Total (excluding pergolide Sulfoxide) |
|---|---|---|---|
| 0 Mo. | 104.6 | 2.0 | 0.1 |
| 3 Mo. | 100.6 | 3.6 | <0.1 |

TABLE 5

Stability study of 1.0 mg pergolide tablets manufactured according to the principles of the invention.

| Interval | Assay (%) | Degradation Products (%) Pergolide Sulfoxide | Degradation Products (%) Total (excluding pergolide Sulfoxide) |
|---|---|---|---|
| 0 Mo. | 103.3 | 0.1 | 0.4 |
| 3 Mo. | 99 | <0.05 | <0.1 |

TABLE 6

Permax ® (1.0 mg)

| Interval | Assay (%) | Degradation Products (%) Pergolide Sulfoxide | Degradation Products (%) Total (excluding pergolide Sulfoxide) |
|---|---|---|---|
| 0 Mo. | 103.8 | 0.9 | 0.1 |
| 3 Mo. | 98.1 | 1.9 | 0.1 |

EXAMPLE 2

Dry Granulation

| Each 0.05 mg pergolide tablet contains: | |
|---|---|
| Pergolide Mesylate | 0.065 mg* |
| Lactose Monohydrate NF | 117.835 mg |
| Microcrystalline Cellulose NF | 60.0 mg |
| Pregelatinized Starch NF | 30.0 mg |
| Sodium Starch Glycolate NF | 30.0 mg |
| Magnesium Stearate NF | 2.0 mg |
| Color Ferric Oxide NF | 0.1 mg |
| TOTAL | 240.0 mg |

*Equivalent to 0.05 mg Pergolide base.

Pergolide mesylate was mixed in a suitable container with lactose monohydrate microcrystalline cellulose, pregelatinized starch, sodium starch glycolate, color ferric oxide and ⅓ of the magnesium stearate quantity. The powder mixture was compressed in a slug tableting machine. The slug tablets were milled and mixed with the rest of the magnesium stearate. The powder mixture was compressed into oval shaped tablets on a rotary tableting machine (batch size 140,000 tabs.) Analytical results were as follows:

Uniformity of content: 97.6%; RSD 3.5%
Uniformity of blend: 97.5%; RSD 1.0%

Stability studies were initiated at accelerated conditions (40° C. at 75% relative humidity for three months). The results are tabulated in Table 7, 8 and 9.

TABLE 7

Stability of 0.05 mg pergolide dry tablets.

| Interval | Assay (%) | Degradation products (%) (Pergolide sulfoxide) | Degradation products (%), total (excluding pergolide sulfoxide) |
|---|---|---|---|
| 0 Mo. | 98.8 | 0.5 | <0.1 |
| 3 Mo. | 91.4 | 2.4 | <0.1 |

TABLE 8

Stability of 0.25 mg Pergolide dry tablets.

| Interval | Assay (%) | Degradation Products (%) (Pergolide Sulfide) | Degradation Products (%), total excluding pergolide sulfide. |
|---|---|---|---|
| 0 Mo. | 96.2 | 0.1 | <0.1 |
| 3 Mo. | 95.0 | 0.8 | <0.1 |

TABLE 9

Stability of 1 mg pergolide dry tablets.

| Interval | Assay (%) | Pergolide Products (% pergolide sulfoxide) | Degradation Products (%), total excluding pergolide sulfoxide |
|---|---|---|---|
| 0 Mo. | 97.0 | <0.1 | <0.1 |
| 3 Mo. | 96.2 | 0.2 | <0.1 |

What is claimed is:

1. A method for manufacturing pergolide mesylate resistant to degradation when exposed to light, the method comprising:
    forming a powder mixture having lactose monohydrate, microcrystalline cellulose, pregelatinized starch, sodium starch, glycolate;
    dissolving pergolide mesylate in water and alcohol to form a pergolide mesylate solution;
    forming a wet granulation by adding the pergolide mesylate solution to the powder mixture;
    drying the wet granulation to form dry granulate;
    milling the dry granulate to form milled granulate;
    mixing magnesium stearate with milled granulate to form a blend.

2. The method of claim 1, wherein pergolide mesylate is dissolved in water and alcohol having a ratio of 1 to 3.

3. The method of claim 2, wherein said drying step is carried out in a fluid bed drier.

4. The method of claim 3, wherein the fluid be dryer uses an airflow of 200 to 500 m³/h/kg.

5. The method of claim 1, further comprising the step of compressing said blend into tablets.

6. A pergolide mesylate composition as produced according to claim 1.

7. A method for manufacturing pergolide mesylate which is resistant to degradation, the method comprising:
    forming a powder mixture having pergolide mesylate, lactose monohydrate, microcrystalline cellulose, pregelatinized starch, sodium starch glycolate, color ferric oxide and magnesium stearate;
    compressing the powder mixture into at least one tablet;
    milling the at least one tablet to form a powder; and
    mixing the milled powder with magnesium stearate to produce stable pergolide mesylate.

8. The method of claim 7, wherein the step of compressing the powder mixture is accomplished by a rotary tableting machine.

9. The method of step 7, further comprising compressing the stable pergolide mesylate into tablets.

10. The method of claim 7, wherein the stable pergolide mesylate initially contains less than 0.5% pergolide sulfoxide.

11. A pergolide mesylate composition as produced according to claim 7.

12. A method for manufacturing pergolide mesylate in the absence of a stabilizing agent, the method comprising:
    providing a powder mixture having at least one of lactose monohydrate, microcrystalline cellulose, pregelatinized starch, sodium starch, glycolate;
    forming a solution of pergolide mesylate in water and alcohol to form a pergolide mesylate solution;
    forming a wet granulation by adding the pergolide mesylate solution to the powder mixture;
    drying the wet granulation to form dry granulate;
    milling the dry granulate to form milled granulate;
    mixing magnesium stearate with milled granulate to form a blend.

13. A method for manufacturing pergolide mesylate composition which is resistant to degradation, the method comprising:
    forming a powder mixture having pergolide mesylate, at least one filler, at least one disintegrant and at least one lubricant;
    compressing the powder mixture into at least one tablet;
    milling the at least one tablet to form a powder;
    mixing the milled powder with magnesium stearate to produce stable pergolide mesylate;
    wherein the pergolide mesylate composition initially contains less than 0.5 wt. % pergolide sulfoxide and after three months of storage at 40° C. and 75% relative humidity contains less than 2.4 wt. % pergolide sulfoxide.

14. A pergolide mesylate composition as produced according to claim 13.

15. The method of claim 13, wherein the stable pergolide mesylate initially contains less than 0.3% pergolide solfoxide.

16. A method for manufacturing pergolide mesylate composition which is resistant to degradation, the method comprising:
    forming a powder mixture having pergolide mesylate, at least one filler selected from the group consisting of lactose monohydrate, at least one disintegrant selected from the group consisting of pregelatinized starch and sodium starch glycolate, and at least one binder;
    compressing the powder mixture into at least one tablet;
    milling the at least one tablet to form a powder; and
    mixing the milled powder with magnesium stearate to produce stable pergolide mesylate.

17. The method of claim 16, wherein the at least one binder is microcrystalline cellulose.

18. A pergolide mesylate composition as produced according to claim 16.

19. A method for manufacturing pergolide mesylate oral dosage which is resistant to degradation, the method comprising:

forming a powder mixture having pergolide mesylate and at least one additive selected from the group consisting of a filler, a binder, a diluent and a disintegrant;

wherein the oral dosage initially contains less than 0.5 wt. % pergolide sulfoxide and after three months of storage at 40° C. and 75% relative humidity contains less than 2.4 wt. % pergolide sulfoxide.

20. The method of claim 19, wherein the dosage initially contains less than 0.1 wt. % pergolide sulfoxide and after three months of storage at 40° C. and 75% relative humidity contains less than 0.8 wt. % pergolide sulfoxide.

21. The method of claim 19, wherein the dosage initially contain less than 0.1 wt. % pergolide sulfoxide and after three months of storage at 40° C. and 75% relative humidity contains less than 0.2 wt. % pergolide sulfoxide.

22. A pergolide mesylate composition as produced according to claim 19.

* * * * *